(12) United States Patent
Angstrom et al.

(10) Patent No.: US 7,708,720 B1
(45) Date of Patent: May 4, 2010

(54) CATHETER TERMINUS PROTECTIVE COVER

(75) Inventors: Jane Angstrom, Danvers, MA (US); Nicholas R. Powley, Weston, MA (US)

(73) Assignee: Janik Medical, Inc., St. Paul, MN (US)

( * ) Notice: Subject to any disclaimer, the term of this patent is extended or adjusted under 35 U.S.C. 154(b) by 1092 days.

(21) Appl. No.: 10/989,015

(22) Filed: Nov. 15, 2004

(51) Int. Cl.
*A61M 5/00* (2006.01)
(52) U.S. Cl. ...................... 604/263; 604/174
(58) Field of Classification Search ................ 604/263, 604/174, 180; 128/DIG. 6, DIG. 26
See application file for complete search history.

(56) References Cited

U.S. PATENT DOCUMENTS

| | | | | |
|---|---|---|---|---|
| 4,490,141 A | * | 12/1984 | Lacko et al. | 604/180 |
| 4,935,011 A | * | 6/1990 | Hogan | 604/177 |
| 4,973,314 A | * | 11/1990 | Garrett | 604/180 |
| 5,417,668 A | * | 5/1995 | Setzer et al. | 604/263 |
| 6,015,119 A | | 1/2000 | Starchevich | |
| 6,273,873 B1 | | 8/2001 | Fleischer | |
| 6,311,933 B1 | * | 11/2001 | Starchevich | 248/65 |
| 2003/0216694 A1 | * | 11/2003 | Tollini | 604/174 |

* cited by examiner

*Primary Examiner*—Kevin C Sirmons
*Assistant Examiner*—Deanna K Hall
(74) *Attorney, Agent, or Firm*—Faegre & Benson LLP

(57) ABSTRACT

A catheter terminus protective system comprising a base panel having a pair of adjoining flaps, an adhesive patch on at least one of the flaps for securing at least one catheter terminus from which a catheter line extends, the flaps being relatively moveable between secured closed positions in which they form a protective enclosure for the catheter terminus, and free open positions in which they allow manual access to said catheter terminus. An original catheter line extends from the protective enclosure when the flaps are in the closed positions and may be replaced by an alternative catheter line when the flaps are opened. The flaps are constituted by a fluid impermeable facing and a fluid absorbent backing in superposition.

20 Claims, 2 Drawing Sheets

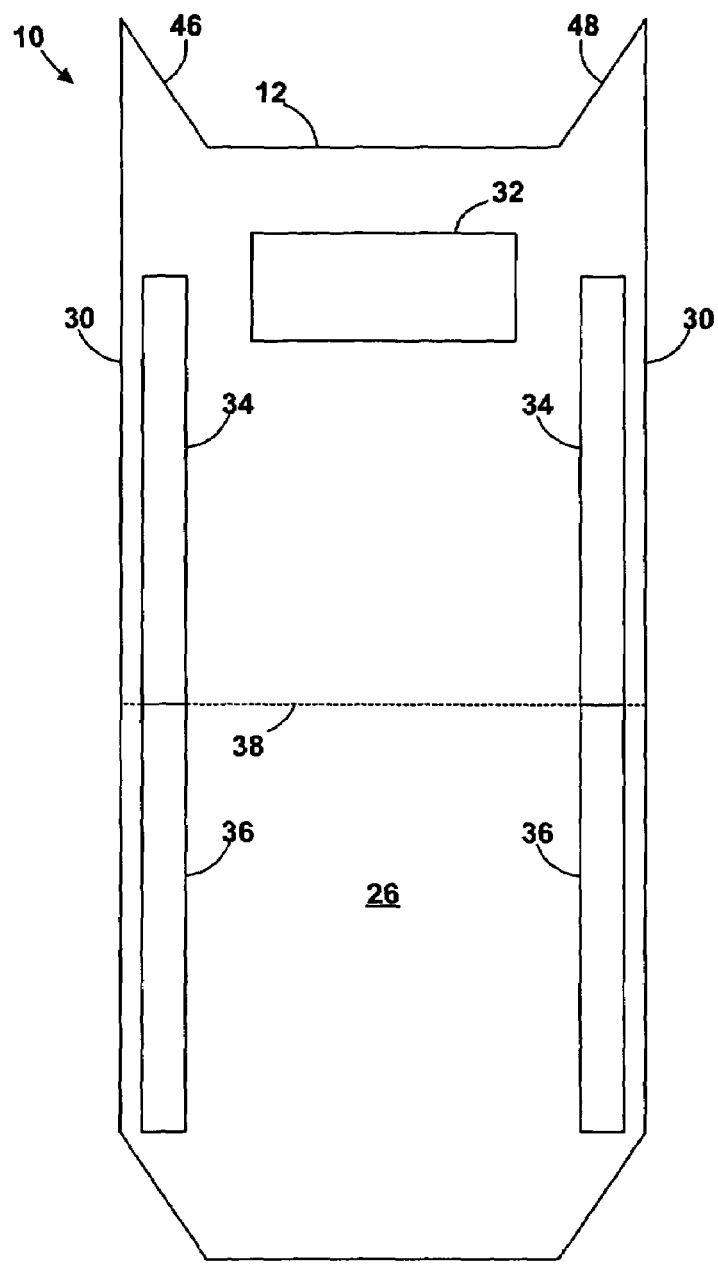 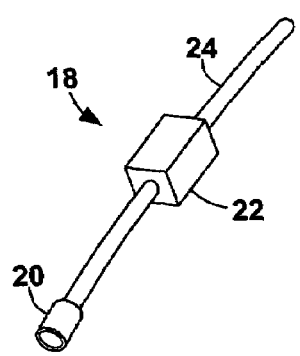
FIG. 1   FIG. 2

CATHETER TERMINUS PROTECTIVE COVER

CROSS-REFERENCES TO RELATED APPLICATIONS

Not Applicable

STATEMENT REGARDING FEDERALLY SPONSORED RESEARCH OR DEVELOPMENT

Not Applicable

REFERENCE TO A SEQUENCE LISTING, A TABLE, OR A COMPUTER PROGRAM LISTING COMPACT DISK APPENDIX

Not Applicable

BACKGROUND OF THE INVENTION

1. Field of the Invention

The present invention relates to medical catheters, which directly access vessels, cavities, and diseased regions of the body to enable intravenous infusion of medications, dialysis, and other medical treatments. More particularly, the present invention relates to the protection of subclavian and interjugular catheters.

2. Description of the Related Art

Typically, subclavian and interjugular catheters have an interior end, which extends during a regimen through a surgical or natural passage into or from the body, and an exterior end, which remains during the regimen outside the body for connection to a fluid source, repository, or processor. During the regimen, while the interior end remains fixed in place in the body, the exterior end may be disconnected and reconnected to a variety of medical devices during a prolonged period. When the exterior end of the catheter is exposed, clamps and injection caps typically keep blood, debris, and medication from leaking out. In order to prevent non-sterile exposure of the injection cap, a technician may wrap gauze pads around the injection caps and may secure the pads with adhesive tape. Although, for ease of explanation, a single catheter line and single injection cap are described hereinafter, multiple catheter lines and injection caps are contemplated.

Problems have arisen because there are no uniform standards for catheter length, configuration, or introduction at the surgical entry. As a result, there is no standard procedure for protecting the clamps, lines, injection caps from contamination or for preventing discomfort of the patient. Poorly wrapped dressings may fall off, leaving the injection caps open to contamination. Manipulating catheter input lines in attempts to remove such a dressing is unwieldy, time consuming, and often requires replacement of the catheter. The configuration and stability of the catheter at the surgical entry has been a matter of chance and has not been based carefully on the comfort of the patient.

BRIEF SUMMARY OF THE INVENTION

The object of the present invention is to provide a cover for a clamp, line, and catheter injection cap (collectively, catheter terminus) in the form of a folder which comprises an elongated base panel and a medial transverse crease that divides the folder into two flaps. With the flaps open, the catheter terminus may be securely positioned by a pressure-sensitive adhesive patch on one of the flaps with the adjoining end of the catheter terminus extending longitudinally and outwardly beyond the extremity of the base panel toward the surgical entry. With the flaps closed, the catheter terminus may be securely enclosed between the flaps by pressure-sensitive adhesive tabs. The catheter terminus may be accessed for disconnecting or reconnecting the catheter to external lines merely by peeling back the pressure-sensitive adhesive tabs and opening the flaps. The flaps, when open, provide a stable base that may be firmly seated on the body of a patient so that manipulation of the catheter terminus will not cause discomfort. The flaps, when closed, provide a sterile environment for the catheter terminus and minimal movement of the line at the surgical entry. Preferably, the base panel is configured from a base section and a pair of longitudinal side sections that are contiguous with the base section. The base section and, optionally, the side sections, are composed of a laminate which comprises a non-absorbent facing for retaining moisture, fluid, and debris, and an absorbent backing for limiting and controlling the escape of the moisture, fluid, and debris when the flaps are opened and closed.

BRIEF DESCRIPTION OF THE DRAWINGS

For a fuller understanding of the nature and object of the present invention, reference is made to the accompanying drawings, wherein:

FIG. 1 is a plan view of a base panel from which the catheter terminus cover of the present invention is configured;

FIG. 2 is a perspective view of a catheter injection cap, clamp and line that is to be protected and manipulated in accordance with the present invention;

DETAILED DESCRIPTION OF THE INVENTION

Figure 3:
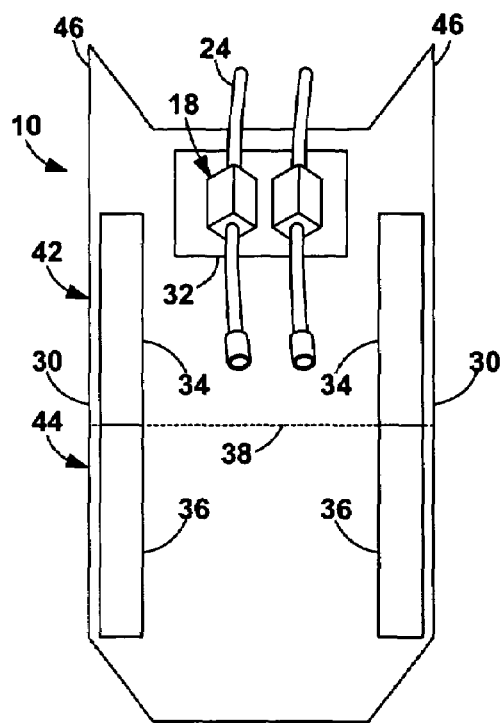
FIG. 3 is a plan view of the blank of FIG. 1 in a beginning stage of formation.

The catheter terminus protective system 10 of the present invention is designed to be inexpensively manufactured, shipped flat, and conveniently configured into the folder of the present invention. Its essential purpose is to provide an enclosure for the protection of a catheter terminus which is at an exterior terminal of a catheter that is being deployed or has been deployed within a surgical or natural passage in a patient's body. Typically, such a catheter terminus 18, shown in FIG. 2, has a rubber plug 20 that may be penetrated by a hollow needle, through which fluid may be transmitted via a tube or line 24 through the aforementioned surgical or natural entry into the patient's body. The line has a clamp 22 for controlling the flow of fluid in the line 24.

As shown in FIG. 1, the catheter terminus protective system 10 of the present invention has an elongated base panel 12 which is comprised of a base section 26, a pair of longitudinal side sections 30, and a patch 32 affixed to the upper part of the base section 26. The patch 32 has a pressure-sensitive adhesive surface by which one or more catheter termini 18 may be secured when the cover is fully configured.

Figure 4:
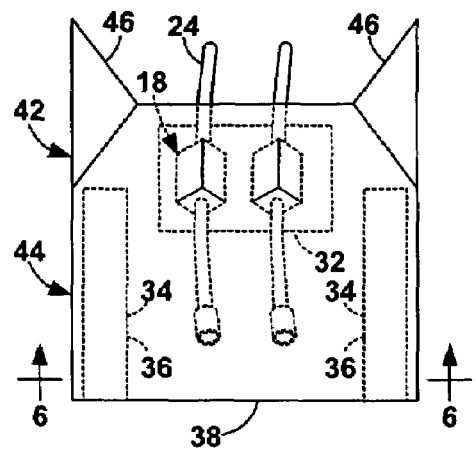
FIG. 4 is a plan view of the blank of FIG. 1 in an intermediate stage of formation.
Figure 6:
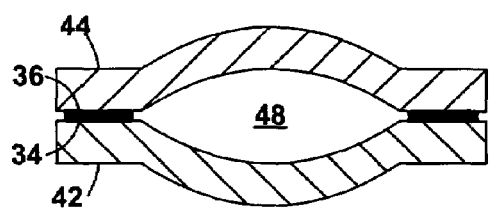
FIG. 6 is an exaggerated cross-section of the fully configured cover taken along the line 6-6 of FIG. 4.

As shown in FIG. 3, the catheter terminus 18 is positioned on the patch 32 with the adjoining end of the tube 24 extending longitudinally and outwardly beyond the extremity of the base section 26 toward the surgical or natural entry in the patient's body. As shown in FIG. 4, the configuration of a cover 10 is begun by folding the base panel 26 along a score or mark 38. The result is an enclosure of two congruent flaps 42, 44, a plan view of which is shown in FIG. 4 and a cross-section of which is shown in FIG. 6. Preferably, each side section 30 has a pair of pressure-sensitive adhesive regions 34, 36. When the base panel 12 is folded, the pressure-sensitive adhesive regions 34, 36 contact each other and form a closure at the side sections 30.

Figure 5:
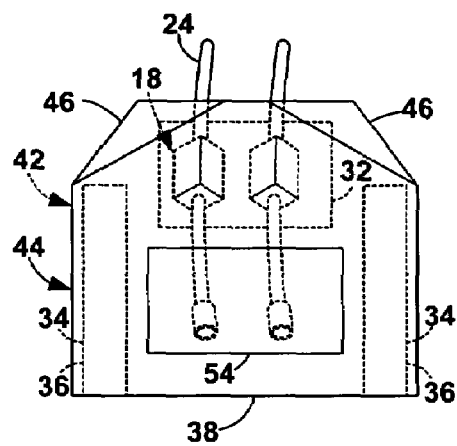
FIG. 5 is a plan view in partial phantom of the finally formed cover of the present invention.

As shown in FIG. 5, the enclosure so formed is secured by a pair of pressure-sensitive adhesive tabs 46, which extend upwardly from the side sections 30 and which are folded over the lower flap 44. With the flaps 42, 44 closed and tabs 46 secure, the catheter terminus 18 is securely contained within a compartment 48 defined by the flaps 42, 44. The catheter terminus 18 within the compartment 48 may be accessed for disconnecting or reconnecting the catheter to external lines merely by peeling back the pressure-sensitive adhesive tabs 46 and opening the flaps 42, 44. The flaps 42, 44, when open, provide a stable seat that may be firmly positioned on the body of a patient so that manipulation of the catheter terminus 18 will not cause discomfort. The flaps 42, 44, when closed, provide a semi-sterile environment for the catheter terminus 18 and minimal movement of the line at the surgical or natural entry into the body.

Figure 7:
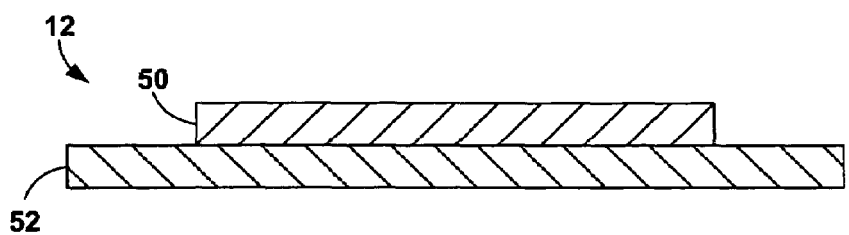
FIG. 7 is a grossly exaggerated cross-sectional view of the laminate of which the base panel of the present invention is composed.

As shown in FIG. 7, the base panel 12 is composed of a laminate which comprises a fluid impermeable facing 50 for retaining moisture, fluid, and debris, and an absorbent backing 52 for enabling efficacious manipulation of the configured folder assemblage by catching and controlling any moisture, fluid, and debris that may escape when the flaps 42, 44 are opened and closed. In one configuration, shown in FIG. 7, the side sections 30 have only the absorbent backing 52 and the base section 26 has both the non-absorbent facing 50 and absorbent backing 52. In another configuration, the entire base panel 12 has both the non-absorbent facing 50 and the absorbent backing 52.

Optionally, one and/or both surfaces of the base panel 26 are impregnated or coated with anti-bacterial and/or other antiseptic materials. Optionally, the outer surface of the lower flap 44 has a writable label 54, as shown in FIG. 5. Optionally, a pressure sensitive adhesive pad with an optional covering is attached to one and/or both surfaces of the base panel 26 for fixing the present device to the patient.

Thus it has been shown and described a catheter cover which satisfies the objects set forth above.

Since certain changes may be made in the present disclosure without departing from the scope of the present invention, it is intended that all matter described in the foregoing specification and shown in the accompanying drawings be interpreted as illustrative and not in a limiting sense.

What is claimed is:

1. A catheter terminus protective system comprising:
   (a) an elongated base panel comprised of a base section having an upper flap and a lower flap delimited by a fold line, longitudinal side sections, and a pair of opposed ends, at least a portion of the side sections having a pressure-sensitive adhesive;
   (b) the base panel being folded at the fold line such that the flaps are congruent and each of the side sections contacts and adheres to itself, wherein a protective enclosure for a catheter terminus is formed, the enclosure having three completely closed sides, one of the enclosed sides being at the fold line, and a fourth side being at an end of the protective enclosure opposite the fold line, the end defining an opening from which the catheter extends from the protective enclosure, wherein the opening has a first size that is substantially equal to a width of the enclosure; and
   (c) a pair of adhesive tabs extending longitudinally from the end adjacent to the upper flap at the fourth side, the tabs being folded over to adhere to the lower flap after the base panel is folded, whereby the opening has a second size that is smaller than the first size such that the catheter terminus is securely contained in a semi-sterile environment within the protective enclosure.

2. The catheter terminus protective system of claim 1, wherein the upper and lower flaps each have an adhesiveless exterior.

3. The catheter terminus protective system of claim 1, further comprising an adhesive pad on an exterior of at least one of the flaps adapted to secure the protective enclosure to a patient.

4. The catheter terminus protective system of claim 1, wherein the first size of the opening is sufficient to receive the catheter terminus through the opening.

5. The catheter terminus protective system of claim 1, wherein the base section is comprised of a fluid impermeable material.

6. The catheter terminus protective system of claim 1, further comprising an adhesive patch on an interior of at least one of the flaps, the patch being adapted to secure the catheter terminus in the protective enclosure.

7. The catheter terminus protective system of claim 1, further comprising a writable label disposed on an exterior of at least one of the flaps.

8. A catheter terminus protective system, comprising:
   (a) an elongated base panel comprising a first flap, a second flap, and a foldable region disposed between the first and second flaps, wherein the first and second flaps are foldable between an open position and a folded position in which the base panel is folded at the foldable region such that the first and second flaps are positioned adjacent to each other;
   (b) each of the first and second flaps comprising:
      (i) a first end opposite the foldable region;
      (ii) first and second longitudinal sides, each extending from the foldable region to the first end; and
      (iii) first and second adhesive strips, wherein the first adhesive strip is positioned adjacent to the first longitudinal side and the second adhesive strip is positioned adjacent to the second longitudinal side;
   (c) a protective enclosure formed of the first and second flaps in the folded position, the protective enclosure comprising:
      (i) a closed end formed by the foldable region of the elongated base panel;
      (ii) a first closed side formed by the first adhesive strips of the first and second flaps adhered to each other;
      (iii) a second closed side opposite the first closed side and formed by the second adhesive strips of the first and second flaps adhered to each other;
      (iv) an adhesiveless exterior formed by the first and second flaps; and
      (v) an opening defined opposite the closed end of the enclosure,
      wherein the protective enclosure is configured to receive a catheter terminus such that a catheter tube coupled to the catheter terminus extends out of the enclosure through the opening; and (d) first and second adhesive tabs extending from the first end of the first flap, wherein the first tab is adjacent to the first side of the first flap and the second tab is adjacent to the second side of the first flap such that the catheter tube extending out of the enclosure is positioned between the first and second adhesive tabs, wherein the first and second tabs are foldable between an open position and a closed position, wherein the closed position comprises the first and second tabs being adhesively attached to the second flap and disposed around the catheter tube such that the catheter terminus is securely contained in a semi-sterile environment within the protective enclosure.

9. The catheter terminus protective system of claim 8, wherein the opening is defined in an end of the protective enclosure.

10. The catheter terminus protective system of claim 8, wherein the opening has an initial size, while the first and second tabs are in the open position, that is substantially equal to a width of the enclosure.

11. The catheter terminus protective system of claim 8, wherein the opening has an initial size, while the first and second tabs are in the open position, that is sufficient to receive a catheter terminus through the opening.

12. The catheter terminus protective system of claim 8, further comprising an adhesive patch disposed within the protective enclosure on one of the first and second flaps, the adhesive patch configured to adhere to the catheter terminus positioned within the protective enclosure.

13. The catheter terminus protective system of claim 8, wherein the base panel is comprised of a fluid impermeable material.

14. The catheter terminus protective system of claim 8, further comprising a writable label disposed on the exterior of at least one of the first and second flaps.

15. The catheter terminus protective system of claim 8, wherein at least one surface of the base panel comprises an anti-bacterial material.

16. A catheter terminus protective system, comprising:
   (a) an elongated base panel comprising a first flap, a second flap, and a foldable region disposed between the first and second flaps, wherein the first and second flaps are foldable between an open position and a folded position in which the base panel is folded at the foldable region such that the first and second flaps are positioned adjacent to each other;
   (b) each of the first and second flaps comprising:
      (i) a first end opposite the foldable region;
      (ii) first and second longitudinal sides, each extending from the foldable region to the first end; and
      (iii) first and second adhesive strips, wherein the first adhesive strip is positioned adjacent to the first longitudinal side and the second adhesive strip is positioned adjacent to the second longitudinal side;
   (c) a protective enclosure formed of the first and second flaps in the folded position, the protective enclosure comprising:
      (i) a closed end formed by the foldable region of the elongated base panel;
      (ii) a first closed side formed by the first adhesive strips of the first and second flaps adhered to each other;
      (iii) a second closed side opposite the first closed side and formed by the second adhesive strips of the first and second flaps adhered to each other;
      (iv) a substantially adhesive-free exterior formed by the first and second flaps; and
      (v) an opening defined in an end of the enclosure opposite the closed end,
      wherein the protective enclosure is configured to receive a catheter terminus such that a catheter tube coupled to the catheter terminus extends out of the enclosure through the opening; and
   (d) first and second adhesive tabs extending from the first end of the first flap, wherein the first tab is adjacent to the first side of the first flap and the second tab is adjacent to the second side of the first flap such that the catheter tube extending out of the enclosure is positioned between the first and second adhesive tabs, wherein the first and second tabs are foldable between an open position and a closed position, wherein the closed position comprises the first and second tabs being adhesively attached to the second flap and disposed around the catheter tube such that the catheter terminus is securely contained in a semi-sterile environment within the protective enclosure,
   wherein the opening has an initial size, while the first and second tabs are in the open position, that is substantially equal to a width of the enclosure.

17. The catheter terminus protective system of claim 16, wherein the base panel is comprised of a fluid impermeable material.

18. The catheter terminus protective system of claim 16, further comprising an adhesive patch disposed within the protective enclosure on one of the first and second flaps, the adhesive patch configured to adhere to the catheter terminus positioned within the protective enclosure.

19. The catheter terminus protective system of claim 16, further comprising a writable label disposed on an exterior of at least one of the flaps.

20. The catheter terminus protective system of claim 16, wherein at least one surface of the base panel comprises an anti-bacterial material.

\* \* \* \* \*